US00PP28346P3

(12) United States Plant Patent
Hillier

(10) Patent No.: US PP28,346 P3
(45) Date of Patent: Aug. 29, 2017

(54) ***WEIGELA* PLANT NAMED 'MANGO'**

(50) Latin Name: *Weigela middendorffiana*
Varietal Denomination: Mango

(71) Applicant: John G. Hillier, Hampshire (GB)

(72) Inventor: John G. Hillier, Hampshire (GB)

( * ) Notice: Subject to any disclaimer, the term of this patent is extended or adjusted under 35 U.S.C. 154(b) by 29 days.

(21) Appl. No.: 14/998,504

(22) Filed: Jan. 14, 2016

(65) Prior Publication Data

US 2016/0219776 P1 Jul. 28, 2016

(30) Foreign Application Priority Data

Jan. 23, 2015 (QZ) ..... PBR 2015/0174

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Bethany R. Roahrig; Barbara Campbell; Cochran Freund & Young, LLC

(57) ABSTRACT

A new cultivar of *Weigela* plant named 'Mango' that is characterized by naturally self-branching habit, bright green leaves and pale yellow funnel-shaped flowers which exhibit contrasting deeper yellow throats which become deep orange-red as the flower matures.

2 Drawing Sheets

Genus and species: *Weigela middendorffiana*.
Variety denomination: 'Mango'.

CROSS REFERENCE TO RELATED APPLICATIONS

This application claims the benefit of priority under 35 U.S.C. 119 (f) to the application for European Community Plant Variety Rights which was filed for the instant plant variety on Jan. 23, 2015, File Number 2015/0174.

BACKGROUND OF THE NEW PLANT

The present invention relates to a new and distinct cultivar of *Weigela*, grown as an ornamental plant for use in the garden and landscape. The new cultivar is known botanically as *Weigela middendorffiana* and will be referred to hereinafter by the cultivar name 'Mango'.

Unlike the common pink and red flowered species and cultivars of *Weigela florida*, the yellow-flowered species *Weigela middendorffiana* is rarely encountered in cultivation or in commerce and no cultivars are known to the inventor. Plants of *Weigela middendorfiana* which are raised from seed are variable in height, habit, flower production and flower color.

Commencing in 2006, the inventor sought to develop a cultivar of *Weigela middendorffiana* with desirable commercial characteristics. Each year, the inventor raised new plants from seeds retained from promising plants identified and set aside from previous generations of open pollination. The new cultivar 'Mango' was selected by the inventor in 2011 as a single plant from amongst a crop of mature plants of unnamed *Weigela middendorffiana* (species, unpatented) which were growing at the inventor's nursery in Romsey, Hampshire, United Kingdom. 'Mango' was selected by the inventor for its unique combination of improved branching, plant density, number and arrangement of flowers and, most significantly, the striking deep orange-red coloration exhibited on the throat or lower petals of certain flowers as they mature.

Asexual reproduction by softwood cuttings of the new cultivar 'Mango' was accomplished by the inventor in 2011 at the inventor's nursery in Romsey, Hampshire, United Kingdom. Since that time, the unique characteristics of the new *Weigela* plant have been uniform, stable and reproduced true to type in successive generations of asexual reproduction.

SUMMARY

The following traits have been repeatedly observed and represent the characteristics of the new *Weigela* cultivar 'Mango'. 'Mango' has not been tested under all possible conditions and phenotypic differences may be observed with variations in environmental, climatic and cultural conditions, however, without any variance in genotype.

1. 'Mango' bears pale yellow funnel-shaped flowers.
2. The flowers of 'Mango' exhibit contrasting deeper yellow throats which become deep orange-red as the flower matures.
3. The flowers of 'Mango' are borne in clusters at the terminals and upper axils.
4. 'Mango' commences flowering in April or May according to climate and season. 'Mango' flowers continuously until July.
5. The foliage of 'Mango' is bright green.
6. 'Mango' is naturally self-branching and spreading, achieving when mature a height of 1.5 m and width of 1.0 m.
7. 'Mango' is suitable for use as a garden or landscape plant.
8. 'Mango' grows well in moist well-drained soils in full sun to partial shade.
9. 'Mango' is hardy to USDA Zone 5.

BRIEF DESCRIPTION OF THE PHOTOGRAPHS

The accompanying color photographs illustrate the overall appearance of the new *Weigela* variety 'Mango' showing colors as true as it is reasonably possible to obtain in colored reproductions of this type. Colors in the photographs may differ from the color values cited in the detailed botanical description, which accurately describe the actual colors of the new variety 'Mango'.

Figure 1:
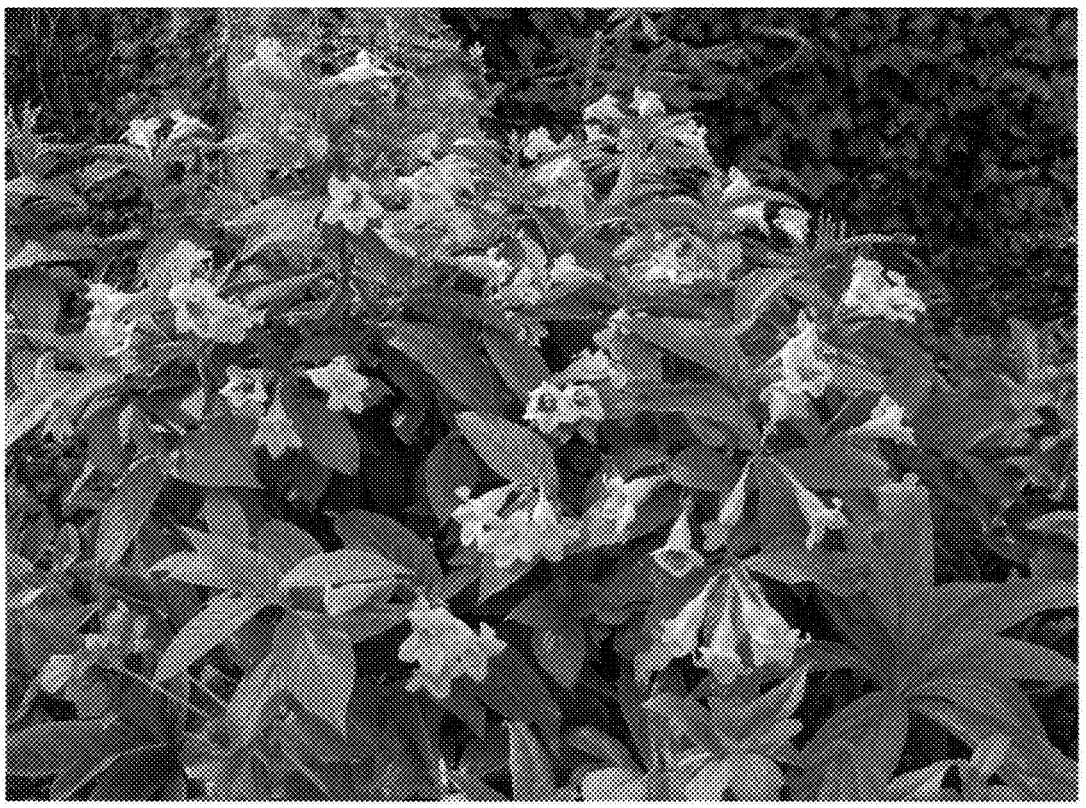
FIG. 1 depicts an entire flowering plant of 'Mango'.
Figure 2:
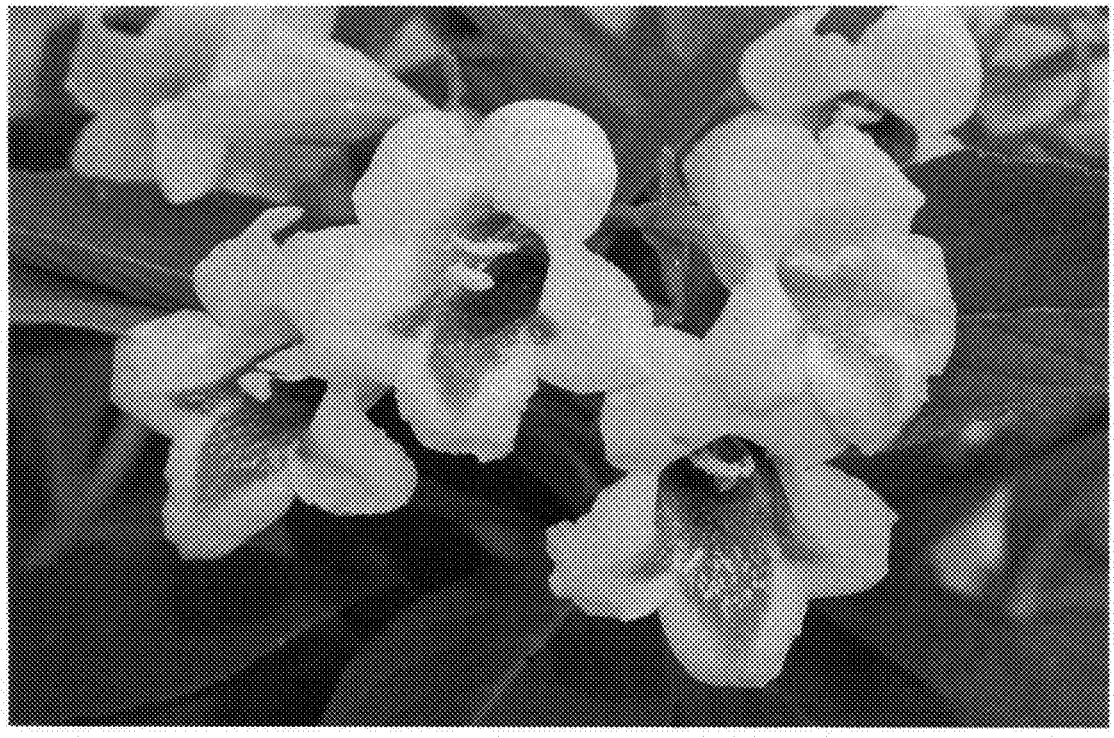
FIG. 2 depicts a close-up view of the flowers of 'Mango'.

Photographs were taken in Romsey, Hampshire, United Kingdom of a one-year old plant which was grown outdoors at the inventor's nursery in Romsey, Hampshire, United Kingdom. No chemicals were used to treat the plants. All photographs were made using conventional techniques and although colors may appear different from actual colors due to light reflectance they are as accurate as possible by conventional photography.

BOTANICAL DESCRIPTION OF THE PLANT

The following is a detailed description of the new cultivar 'Mango'. Data was collected from one-year old plants grown outdoors Romsey, Hampshire, United Kingdom. The color determinations are in accordance with the 2001 edition of The Royal Horticultural Society Colour Chart of The Royal Horticultural Society, London, England, except where general color terms of ordinary dictionary significance are used. No chemicals were used to treat the plants. Growing conditions are typical to other *Weigela*.

Botanical classification: *Weigela*.

*Variety*.—'Mango'.

*Species*.—*middendorffiana*.

Parentage: 'Mango' was selected as an open pollinated seedling raised from unnamed seed of the species *Weigela middendorffiana*.

Plant description:

*Growth habit*.—Initially upright, then branching and spreading as plant matures.

*Use*.—In containers and in the landscape.

*Suitable container sizes*.—1 to 3 gallon containers.

*Dimensions in first year*.—45 cm in height and 35 cm in width.

*Dimensions when mature*.—1.5 m in height and 1.0 m in width.

*Hardiness*.—USDA Zone 5.

*Propagation*.—Stem cuttings.

*Time to initiate roots*.—5 to 6 weeks are required to produce roots on an initial cutting.

*Crop time*.—One year to 18 months are required to produce a finished one-gallon to three-gallon container from a rooted cutting.

*Root system*.—Fibrous.

*Light*.—Plant in full sun or partial shade.

*Soil*.—Plant in moist but well drained soil.

*Type*.—Deciduous shrub.

*Seasonal interest*.—Pale yellow flowers with bright mid-yellow and orange-red throats in spring.

Stem, branches:

*Main stem color*.—200A.

*Branching stems color*.—144C.

*Stem shape*.—Terete.

*Main stem dimensions*.—8 cm to 12 cm in length, 1 cm diameter at soil level.

*Branch stem dimensions*.—20 cm to 25 cm in length, 3 mm to 5 mm in diameter.

*Internode length*.—2 cm to 3 cm.

*Stem surface*.—Strigose, white hairs 1 mm to 2 mm in length.

Foliage:

*Leaf arrangement*.—Opposite.

*Leaf division*.—Simple.

*Leaf shape*.—Narrowly ovate, recurved.

*Leaf dimensions*.—45 mm to 65 mm in length and 18 mm to 25 mm in width.

*Leaf apex*.—Acuminate.

*Leaf base*.—Rounded.

*Leaf margin*.—Finely serrate.

*Leaf venation pattern*.—Pinnate, reticulate.

*Vein color*.—Same color as leaf except midrib 144D.

*Leaf surface* (*abaxial*).—Glabrous. White hairs scattered along veins, hair length 1 mm to 2 mm.

*Leaf surface* (*adaxial*).—Glabrous. White hairs present on most of surface, hair length 1 mm to 2 mm.

*Leaf color* (*adaxial*).—143A.

*Leaf color* (*abaxial*).—144C.

*Leaf attachment*.—Sessile or very short petiolate.

*Petiole dimensions* (*where present*).—2 mm in length and 2 mm in width.

*Petiole color*.—Ranges between 143A and 144C.

Inflorescence:

*Inflorescence form*.—Cymose. Present terminally and in upper leaf axils.

*Quantity of flowers per inflorescence*.—2 to 5.

*Time and duration of flowering*.—Beginning in April or May according to climate and season, lasting until July.

Flowers:

*Flower aspect*.—Salverform.

*Diameter of fully developed flower* (*at flower tube apex*).—25 mm to 28 mm.

*Length of flower*.—35 mm.

*Bud*.—Shape: Ellipsoid. Color: 145C. Dimensions: 20 mm to 25 mm in length, up to 10 mm immediately prior to opening. Surface: Tomentose.

*Bracteoles*.—Location: Paired at the base of peduncle. Description: Narrowly lanceolate, 5 mm to 8 mm in length and 1 mm in width.

*Peduncle*.—Dimensions: 10 mm to 12 mm in length and 3 mm in diameter. Shape: Terete. Color: 144C. Surface: Scattered very short white hairs.

*Calyx, sepals*.—Shape: Funnel-shaped. Calyx diameter: 5 mm. Sepals: 5 in number, unfused. Sepal dimensions: 8 mm to 10 mm in length, 2 mm in width. Sepal color (both surfaces): 144C. Sepal surface (both surfaces): Lightly pubescent.

*Corolla*.—Shape: Salverform. Dimensions: 30 mm in length and 10 mm to 15 mm in width. Surface: Glabrous. Tube color (adaxial surface): 154C at base, then entirely pale cream yellow, between 155A and 4D. Tube color (abaxial surface): Same as adaxial surface except lower surface either mid yellow 14B or deep orange-red 34A and 34B.

*Petals* (*lobes*).—Number: 5, fused. Shape: Equal, orbicular, markedly recurved. Color (both surfaces, except for three lower petals as next): Between 155A and 4D. Color (three lower petals, abaxial surface only): Between 155A and 4D with central splashes either mid yellow 14B or deep orange-red 34A and 34B. Surface texture: Glabrous.

Reproductive organs:

*Number of stamens.*—5, fused at base.

*Dimensions.*—10 mm in length and less than 2 mm in width.

*Filament color.*—4D.

*Anther shape.*—Bifid, elliptical, parallel.

*Anther dimensions.*—3 mm to 4 mm in length and 1 mm in width.

*Anther color.*—155A.

*Pollen color.*—Pale yellow-white.

*Pollen amount.*—Minimal.

*Number of pistils.*—1.

*Style.*—Terete, 20 mm in length and less than 2 mm in width.

*Style color.*—4D.

*Style surface.*—Glabrous.

*Stigma shape.*—Capitate, three-lobed.

*Stigma dimensions.*—Up to 6 mm in width and 3 mm in depth.

*Stigma color.*—155A.

*Ovary.*—Superior, ovoid, 3 mm in length and 2 mm in diameter, color 154C, smooth.

Fruit and seed: None observed to date.

Diseases and pests: No susceptibilities to pests or disease are known.

COMPARISON KNOWN VARIETY

The closest comparison plants known to the inventor are seed-raised plants of the species *Weigela middendorfiana*. Seed-raised plants are variable one from another, are generally looser in habit and bear fewer flowers. Other than seedlings raised and discarded by the inventor, the inventor has not observed any seed-raised plants which bear flowers with the characteristic deep orange-red coloration which is present in the throat and lower petals of 'Mango'.

I claim:

1. A new and distinct cultivar of *Weigela* plant named 'Mango' as described and illustrated herein.

* * * * *